United States Patent [19]

Scherr et al.

[11] 4,052,979

[45] Oct. 11, 1977

[54] JEWELRY AND BRACELET HEARTBEAT MONITOR

[75] Inventors: Mary Ann Scherr; Harry L. Hosterman, both of Akron, Ohio

[73] Assignee: Mary Ann Scherr, Akron, Ohio

[21] Appl. No.: 637,726

[22] Filed: Dec. 4, 1975

[51] Int. Cl.² ............................................. A61B 5/02
[52] U.S. Cl. ............................ 128/2.05 P; 128/2.05 T; 128/2.06 F
[58] Field of Search ............... 128/2.05 P, 2.05 T, 128/2.05 R, 2.06 A, 2.06 F

[56] References Cited

U.S. PATENT DOCUMENTS

| | | | |
|---|---|---|---|
| 2,492,617 | 12/1949 | Boland et al. | 128/2.06 F |
| 2,658,505 | 11/1953 | Sheer | 128/2.05 P |
| 3,138,151 | 6/1964 | Chapman et al. | 128/2.05 P |
| 3,176,681 | 4/1965 | Smith | 128/2.05 P |
| 3,835,837 | 9/1974 | Peek | 128/2.05 P |
| 3,838,684 | 10/1974 | Manuel et al. | 128/2.05 P |
| 3,858,574 | 1/1975 | Page | 128/2.05 P |
| 3,863,626 | 2/1975 | Huber | 128/2.06 F |
| 3,903,873 | 9/1975 | Royal et al. | 128/2.05 P |

*Primary Examiner*—Robert W. Michell
*Assistant Examiner*—Lee S. Cohen
*Attorney, Agent, or Firm*—Oldham & Oldham Co.

[57] ABSTRACT

A device for monitoring the heartbeat of an individual at a pulse point. Fundamentally, the invention comprises two piezoelectric sensors arranged in close parallel relationship with each other and differentially connected to an amplifier circuit. One of the sensors lies over the pulse point of the individual while the other lies therebeside. A rate detector receives the amplified outputs of the sensors and determines the pulse rate from the heart. If this rate exceeds a predetermined level, a signal is passed to enable an oscillator of audible frequency; the output of the oscillator being connected to any earphone speaker to produce a warning sound.

8 Claims, 1 Drawing Figure

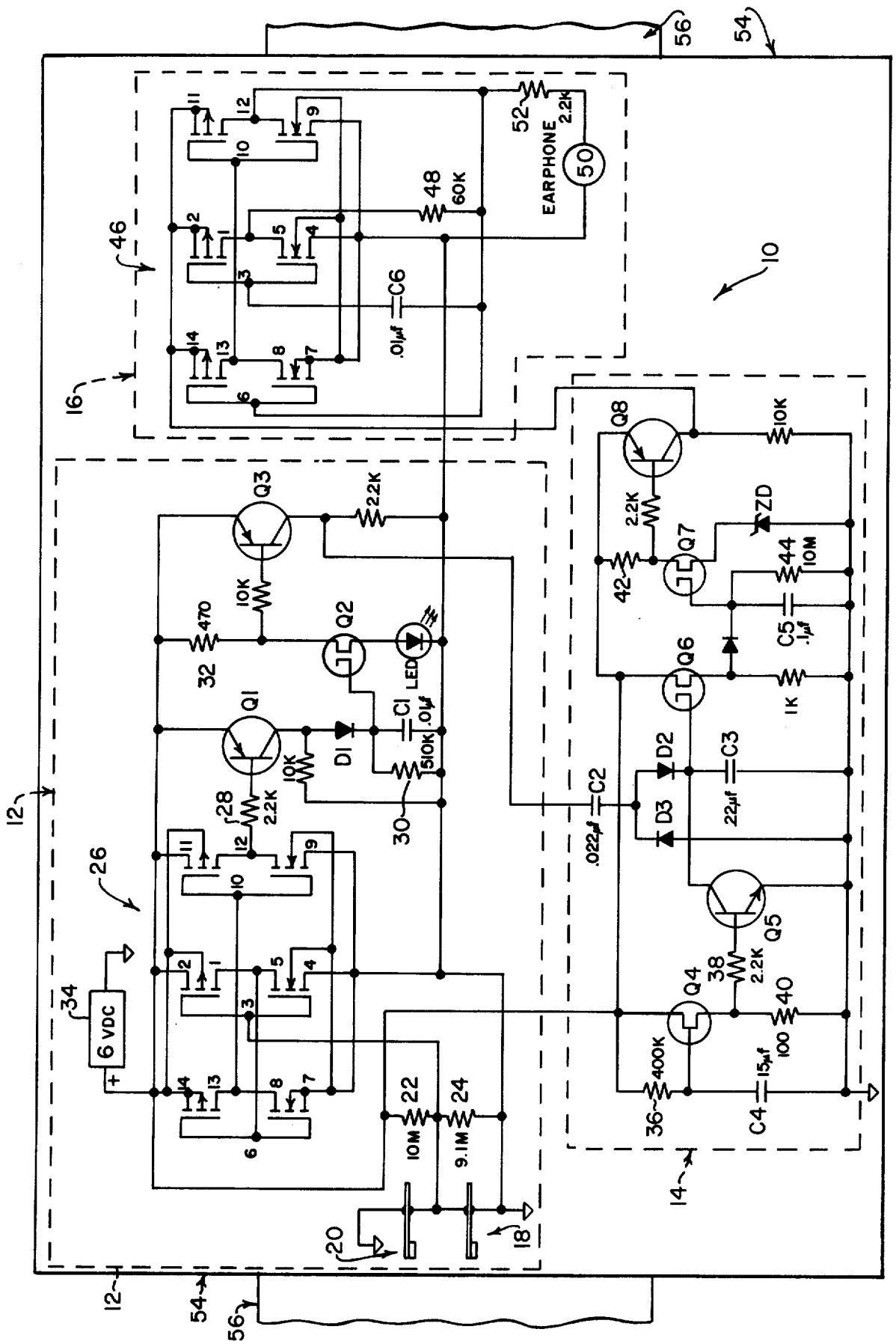

JEWELRY AND BRACELET HEARTBEAT MONITOR

BACKGROUND OF THE INVENTION

Those people who are aware of heart conditions or have experienced coronary problems often times find it desirable to monitor their rate of heart pulsation. If the heartbeat is of an excessive rate, such rate being dictated by their physician, it becomes advisable for them to either curtail their activities, take appropriate medication, or contact their physicial. Heretofore the continual monitoring of one's heartbeat while allowing the individual to carry on a normal life style unencumbered by complex monitoring devices have been virtually unknown. Even those monitors which can be used for such purposes have been extremely expensive as well as being unsightly and burdensome.

OBJECTS OF THE INVENTION

Consequently, it is an object of the instant invention to present a bracelet heartbeat monitor for continually monitoring the heartbeat of the wearer and being operative to emit an audible signal when such heartbeat rate exceeds a critical level.

Still another object of the invention is to present a bracelet heartbeat monitor which is of small physical size and which takes on the appearance of a piece of jewelry on the wearer's body.

Yet another object of the invention is to present a bracelet heartbeat monitor which is relatively inexpensive to construct, highly accurate in operation, impervious to the effects of motions of the wearer other than the heartbeat, and which may be constructed in a small bracelet-like package from state of the art components.

These objects and other objects which will become apparent as the detailed description proceeds are achieved by: a device for monitoring the heartbeat of an individual at a pulse point and for emitting a warning signal when such heartbeat exceeds a critical rate, comprising: sensor means for placement at the pulse point to produce an electrical signal upon sensing of each heartbeat; a rate detector connected to the sensor means for receiving electrical signals and producing an output if the frequency of the electrical signals exceeds a fixed level; and alarm means connected to the rate detector for exciting an alarm upon receipt of the output.

DESCRIPTION OF THE DRAWINGS

For a complete understanding of the objects and structure of the invention reference should be had to the following detailed description and accompanying drawing wherein there is shown a schematic diagram of the circuitry comprising a preferred embodiment of the invention.

DETAILED DESCRIPTION OF PREFERRED EMBODIMENT

With reference now to the drawing, a detailed understanding of the structure of the invention may be acquired by reference to the circuitry designated generally by the numeral 10. It will be noted that this circuitry comprises three basic subcircuits; a sensor/amplifier 12, a rate detector 14, and an oscillator/alarm circuit 16. While each of these elements will be elaborated upon hereinafter, it should be briefly noted that the sensor/amplifier 12 senses the actual physical perturbation caused by one's pulse within the body and passes a signal for each such pulse to the rate detector 14. This circuit then counts the number of such signals received over a fixed time duration, thus determining the pulse rate. If this rate exceeds a particular predetermined level, a signal is passed to the oscillator/alarm circuit 16 whereby an audible tone or other signaling indicia is made of the existent critical pulse rate. It would be well to note at this point that although the physical sensing of the wearer's pulse may be made anywhere on the body, it is anticipated that unit 10 be worn over a standard pulse point such as the wrist, neck, ankle or the like.

Referring now particularly to the structure of the sensor/amplifier 12, it can be seen that the same preferably incorporates two sensors 18,20. While these sensors may be of any suitable nature for achieving the objects of the invention, it is preferable that they be piezo-electric sensors constructed of any suitable material, such as lead zirconate. As is well known to those skilled in the art, such sensors are operative to generate an electric moment by a change of stress applied to the solid material; the stress in this instance being the perturbation caused by a heartbeat. Suffice it to say that physical stresses or impulses sensed by either of the sensors 18,20 results in a low level electrical output signal from the effected sensor. It should be noted in the drawing that the sensors 18,20 are differentially connected and are maintained within a compartment 54 in parallel relation to each other such that one of the sensors 18,20 lies over the wearer's pulse point, while the other lies beside the same. The sensors 18,20 maintain this position relative to the pulse point by means of an appropriate band or strap 56 connected to the compartment 54. By aesthetically designing the elements 54,56, the apparatus wil maintain the appearance of a bracelet or other piece of jewelry on the wearer. By providing this physical arrangement and by further providing for differential electrical interconnection, the output of the sensor arrangement 18,20 is null if both sensors sense the same motion (for example, simple body movement of the wearer), but produces an output signal when only one of the sensors senses a motion (the perturbation of a heartbeat). Thus, by virtue of a unique physical and electrical interconnection of the sensors 18,20, there is provided means for negating the effects of motion or stresses applied to the sensors other than those caused by the heart.

The differential output of the sensors 18,20 is applied through the voltage divider 22,24 to the input of an amplifier circuit 26. While the amplifier 26 may be of any appropriate character, it is preferred that the same be an RCA part no. CA3600E, which includes three CMOS amplifiers as shown. The high impedance input of CMOS circuitry is quite receptive to the low voltage output signals from the sensors 18,20. Suffice it to say that the amplifier 26 amplifies the sensor output signal and applies the same to the base of the transistor Q1 via the resistor 28. The negative going output signal of the amplifier 26 gates the transistor Q1 into conduction and charges the capacitor C1 through the diode D1. The charge on the capacitor C1 gates the field effect transistor (FET) Q2 into conduction and maintains such conduction for the discharge time of the capacitor C1 through the resistor 30. Of course, such time is determined by the RC time constant of the components selected. Thus, the FET Q2 conducts on each heartbeat pulse passing current through the resistor 32 and the light emitting diode (LED). By appropriately selecting the time constant of capacitor C1 and resistor 30 such that the on time of the LED is approximately fifty percent of the period of a normal pulse rate, it should be appreciated that even a short pulse will be made visible on every heartbeat.

With the FET Q2 conducting, the voltage drop across the resistor 32 gates the transistor Q3 into conduction and presents a square wave pulse output as the collector on each heartbeat. If the voltage source available to the unit 10 is a 6 volt source, it should be appreciated that the square wave output at the collector of Q3 would be a positive going pulse of approximately 5 volts. It should, of course, be conceived that a 6 volt supply 34 could be readily created by the series connecion of four one and one-half volt mercury cells as are standardly used in hearing aid devices.

The square wave output of Q3 is then passed to the rate detector circuit 14 and is coupled across the coupling capacitor C2 to a large charging capacitor C3. The capacitor C3 is charged a fixed amount of each heartbeat pulse and the charge is retained there because of the isolation provided by diode D2, the high impedence input of the gate of FET Q6, and the normally non-conductive state of transistor Q5. Thus, the capacitor C3 acts as a counter, being incremented one count on each heartbeat. The diode D3 serves to provide a discharge path for the capacitor C2 to allow the capacitor to operate uniformily for coupling purposes. While the charge on capacitor C3 is building up via the pulsing of transistor Q3, the capacitor C4 is being charged from the voltage supply source 34 through resistor 36. After an amount of time dependent upon the value of resistor 36 and capacitor C4, the capacitor C4 is charged to a level sufficient to cause the unijunction transistor Q4 to conduct. The consequent voltage at the junction of resistors, 38,40 turns on transistor Q5 which is operative to discharge the capacitor C3. Similarly, the capacitor C4, which acts as a timer, is discharged through Q4 and the time period begins anew with the charging of capacitors C3 and C4 as aforementioned.

Should the rate of fixed amplitude pulses emitted from Q3 exceed a particular level, that level being sufficient to charge the capacitor C3 above a level set by zener diode ZD, before the discharge of the capacitor C3 via Q5, the FET Q6 will be gated on thus charging capacitor C5 and gating Q7 into condition. The resultant current through resistor 42 will turn Q8 on. With Q8 conducting, a positive voltage signal is sent to the positive voltage inputs of the oscillator/alarm circuit 16 to indicate that the heartbeat pulse rate exceeds a critical level. The oscillator circuit 16 will continue with the associated warning alarm for a period of time determined by the RC time constant of capacitor C5 and discharge resistor 44. Preferably, this time duration is for about five seconds. After this time the discharged capacitor C5 allows FET Q7 to turn off thus gating off transistor Q8 and removing the positive voltage source or actuation signal from the oscillator/alarm circuit 16. It should be readily appreciated then that the critical pulse rate is determined by proper selection of capacitors C2 and C3, zener diode ZD acting as a threshold detector, and the RC time constant of resistor 36 and capacitor C4. The duration of alarm actuation is controlled by capacitor C5 and resistor R44.

The oscillator/alarm circuit 16, which receives the actuation signal from the collector of transistor Q8, comprises an oscillator circuit 46 which is again comprised of the same circuit as the element 26 aforementioned. Specifically, by properly interconnecting the three CMOS amplifiers in the package 46 with appropriate feedback as is well known in the art, one may readily construct an oscillator circuit which continues in oscillation during the period of an enabling signal as supplied from Q8. The interconnection of the amplifiers to achieve such function is shown in the drawing and not elaborated upon herein. The frequency of the oscillator is determined by the resistor 48 and capacitor C6 and is preferably set at an audible level such as 2khz. An earphone such as a normal hearing aid piece 50 with associated current limiting resistor 52 is provided across the output of the oscillator to make the signal audible. Of course, the strength of the tone is determined by the value of the resistor 52 which might be a potentiometer for adjustability.

Thus, it can be seen that the wearer of the apparatus 10 may note generally from the function of the LED his general heart pulse rate and be advised by an audible tone when such rate exceeds a critical level as determined by his physician and electrically set by means of the aforementioned components of the circuit 14. Effectively then a circuit 12 senses and amplifies heartbeats while the rate detector 14 monitors the same on a timed basis and determines a pulse rate therefrom. This circuit 14 is operative, if such rate exceeds a critical level, to emit an actuating signal to an oscillator/alarm circuit 16 for purposes of warning the wearer of the existent situation.

Thus it can be seen that the objects of the invention have been achieved by the structure and apparatus discussed hereinabove.

While in accordance with the patent statutes only the best mode and preferred embodiment of the invention has been presented and described in detail, it is to be understood that the invention is not limited thereto or thereby. Consequently, for an appreciation of the true scope and breadth of the invention, reference should be had to the appended claims.

What is claimed is:

1. A device for monitoring the heartbeat of an individual at a pulse point and for emitting a warning signal when such heartbeat exceeds a critical rate, comprising:
   first and second piezo-electric sensor means differentially connected to each other for presenting an output signal characteristic of the heartbeat;
   an amplifier means connected to said first and second sensor means for receiving and amplifying said output signal;
   a squaring circuit means connected to said amplifier means for creating a square wave pulse on receipt of the amplified signal from said amplifier means;
   a first charging capacitor means connected to said squaring circuit means for receiving said square wave pulses and charging in relation to the receipt of such pulses;
   a voltage supply;
   a second charging capacitor means connected to said voltage supply and charging at a predetermined rate;
   an alarm circuit means for creating an alarm signal upon excitation; and
   an alarm excitation circuit means interconnected among said first and second charging capacitor means and said alarm circuit means for exciting said alarm circuit means if said first charging capacitor means reaches a first level of charge before said second charging capacitor means reaches a second level of charge.

2. The device as recited in claim 1 which further includes a first transistor means interconnected between said first and second capacitor means for discharging said first capacitor means if said second capacitor means reaches said second level of charge before said first capacitor means reaches said first level of charge.

3. The device recited in claim 2 wherein said alarm excitation circuit means includes a first field effect transistor connected to said first capacitor means, a third capacitor means connected to and charged through said first field effect transistor, a second field effect transistor connected to and gated by said third capacitor means, and a second transistor connected to and controlled by said second field effect transistor.

4. The device as recited in claim 1 wherein said squaring circuit means includes a third capacitor means in parallel connection with a resistor for charging under control of said amplified signal, a field effect transistor connected to said third capacitor means and gated into conduction for a period of time determined by the discharge rate of said third capacitor means through said resistor, and a transistor connected to and controlled by said field effect transistor.

5. The device as recited in claim 4 which further includes light emitting diode means connected to and controlled by said field effect transistor for emitting a light signal indicative of the heart pulse rate.

6. The device as recited in claim 5 wherein said first and second piezo-electric sensor means are physically arranged in adjacent parallel relationship to each other, said first sensor means being adapted for positioning directly over the pulse point with said sensor means being positioned immediately therebeside.

7. The device as recited in claim 6 which further includes a case containing said first and second sensor means and a strap about said case for securing said sensor means in a fixed position upon the individual's body.

8. The device as recited in claim 7 wherein said alarm circuit means comprises an oscillator and a speaker connected to said oscillator.

* * * * *